US010039707B2

(12) United States Patent
Kerl et al.

(10) Patent No.: US 10,039,707 B2
(45) Date of Patent: Aug. 7, 2018

(54) OXIDATION DYEING AGENT HAVING SPECIFIC NON-IONIC SILICONE POLYMERS

(71) Applicant: Henkel AG & Co. KGaA, Duesseldorf (DE)

(72) Inventors: Sylvia Kerl, Hamburg (DE); Susanne Bietz, Elmshorn (DE)

(73) Assignee: Henkel AG & Co. KGaA (DE)

(*) Notice: Subject to any disclaimer, the term of this patent is extended or adjusted under 35 U.S.C. 154(b) by 0 days.

(21) Appl. No.: 15/430,090

(22) Filed: Feb. 10, 2017

(65) Prior Publication Data
US 2017/0151162 A1 Jun. 1, 2017

Related U.S. Application Data

(63) Continuation of application No. PCT/EP2015/064352, filed on Jun. 25, 2015.

(30) Foreign Application Priority Data

Aug. 14, 2014 (DE) ........................ 10 2014 216 202

(51) Int. Cl.
| | | |
|---|---|---|
| *A61Q 5/10* | (2006.01) | |
| *A61K 8/894* | (2006.01) | |
| *A61Q 5/06* | (2006.01) | |
| *A61K 8/893* | (2006.01) | |
| *A61K 8/44* | (2006.01) | |
| *A61K 8/41* | (2006.01) | |

(52) U.S. Cl.
CPC ............... *A61K 8/894* (2013.01); *A61K 8/41* (2013.01); *A61K 8/442* (2013.01); *A61K 8/893* (2013.01); *A61Q 5/065* (2013.01); *A61Q 5/10* (2013.01); *A61K 2800/4322* (2013.01); *A61K 2800/4324* (2013.01)

(58) Field of Classification Search
CPC . A61Q 5/10; A61K 8/41; A61K 8/447; A61K 8/893; A61K 2800/4324; A61K 2800/4322
USPC ............................................................. 8/405
See application file for complete search history.

(56) References Cited

U.S. PATENT DOCUMENTS

| | | | | |
|---|---|---|---|---|
| 6,156,076 A | * | 12/2000 | Casperson | ............... A61K 8/22 424/70.11 |
| 2002/0144356 A1 | | 10/2002 | Kawai et al. | |
| 2009/0081146 A1 | | 3/2009 | Fukuhara et al. | |
| 2010/0017971 A1 | | 1/2010 | Chiba et al. | |
| 2010/0229314 A1 | | 9/2010 | Takiguchi | |
| 2011/0271465 A1 | * | 11/2011 | Yamaguchi | ............... A61K 8/49 8/407 |
| 2013/0125317 A1 | | 5/2013 | Rudolph et al. | |
| 2013/0156716 A1 | | 6/2013 | Yontz | |
| 2014/0190999 A1 | * | 7/2014 | Weser | ....................... A61K 8/42 8/405 |

FOREIGN PATENT DOCUMENTS

| | | |
|---|---|---|
| EP | 0547790 B1 | 8/1995 |
| EP | 2329809 A1 | 6/2011 |
| EP | 2556816 A2 | 2/2013 |
| EP | 2559456 A2 | 2/2013 |

OTHER PUBLICATIONS

STIC Search Report dated Mar. 31, 2017.*
English abstract (Oct. 18, 2017) of the Japanese Patent No. JP 2005029508 A.*
PCT International Search Report (PCT/EP2015/064352) dated Sep. 17, 2015.
Database GNPD Mintel, "Ammonia Free Permanent Colouring Cream", XP002742642, Database Accession No. 1044299, 2009.
Database GNPD Mintel, "Fortifying Hair Colour", XP002742644, Database Accession No. 1176630, 2009.
Database GNPD Mintel, "Hair Colorant", XP002742643, Database Accession No. 1984658, 2013.
Database GNPD Mintel, "Anti-Grey Color Gel", XP002742641, Database Accession No. 2574083, 2014.

* cited by examiner

*Primary Examiner* — Eisa B Elhilo
(74) *Attorney, Agent, or Firm* — P. Scott Smith

(57) ABSTRACT

The invention relates to a cosmetic agent for dyeing keratin fibers, in particular human hair, containing at least one specific non-ionic silicone polymer and at least one oxidation dye intermediate and/or one direct dye, wherein the use of the at least one non-ionic silicone polymer leads to improved care of the keratin fibers together with extremely low color shift. The invention further relates to a corresponding packaging unit (kit of parts) and to a method for dyeing keratin fibers. Finally, the invention relates to the use of the cosmetic agent according to the invention to care for keratin fibers while at the same time minimizing the color shift.

12 Claims, No Drawings

OXIDATION DYEING AGENT HAVING SPECIFIC NON-IONIC SILICONE POLYMERS

FIELD OF THE INVENTION

The present invention generally relates to cosmetic agents for dyeing keratinic fibers, which include special nonionic silicone polymers.

Furthermore, the present invention relates to a packaging unit (kit of parts), containing a cosmetic agent of the invention and an oxidizing agent preparation.

Moreover, the present invention relates to a method for dyeing keratinic fibers with use of a cosmetic agent of the invention as well as an oxidizing agent preparation.

Lastly, the present invention relates to the use of a cosmetic agent of the invention or a packaging unit of the invention to improve the care of keratinic fibers while simultaneously minimizing the color shift.

BACKGROUND OF THE INVENTION

Human hair is treated in many ways today with hair cosmetic preparations. These include, for instance, cleansing the hair with shampoos, the care and regeneration with rinses and treatments, and bleaching, coloring, and shaping the hair using dyes, tints, waving compositions, and styling preparations. In this connection, agents for modifying or nuancing the color of head hair play an important role. Apart from bleaching compositions which bring about an oxidative lightening of the hair by breaking down natural hair dyes, oxidative hair dyeing is of major importance in the field of hair color modification.

So-called oxidation dyeing agents are used for permanent, intensive colors with suitable fastness properties. Such dyeing agents customarily include oxidation dye precursors, also called developer components and coupler components. The developer components form the actual dyes under the influence of oxidizing agents or atmospheric oxygen with one another or during coupling with one or more coupler components. For natural-looking colors, it is customarily necessary to use a mixture of a relatively large number of oxidation dye precursors (designated as ODP hereafter); in many cases, direct dyes (designated as DD hereafter) are used, furthermore, for providing nuances.

In order to stabilize the dye precursors during storage and to accelerate the reaction during the oxidative application, oxidative dyeing agents mostly have an alkaline pH, which is adjusted with alkalizing agents, such as alkanolamines, ammonia, or inorganic bases.

The aforementioned oxidation dye precursors (ODP) and alkalizing agents are typically incorporated into a cosmetically suitable carrier, for example, a cream or a gel. The carrier assures a homogeneous distribution and a sufficient residence time of the oxidative dyeing agent on the hair.

Commercial oxidation dyeing agents are generally formulated in product series, which comprise a standardized carrier, which can be combined with the nuance-specific ODP combination and alkalizing agents as much as possible without limitation.

Consumers usually may obtain an indication of the hair color achievable with a hair dyeing agent from the packaging of the hair dyeing agent and/or a color chart enclosed in the packaging. It is very important for the consumer in this case that the result of the dyeing matches as accurately as possible the color indicated by the manufacturer.

Hair dyeing agents are therefore tested comprehensively and extensively in regard to the achievable color and a plurality of application properties before introduction on the market. However, these tests always consider the interactions between ODP and optionally DD and the standardized carrier only for a specific standardized carrier. The manufacturer frequently wishes to match a hair dyeing agent series selectively to the special requirements of specific consumer groups by adding suitable active or care substances to the standardized carrier. For example, the addition of one or more care substances with a repairing action would be advisable for consumers with highly damaged hair; the addition of one or more active substances that strengthen the hair structure would be advisable for consumers with fine hair.

The result, however, depends not only on the employed combination of the ODP and optionally DD, but is also particularly influenced by the ingredients of the carrier. For example, the addition of care and/or active substances to the standardized carriers can lead to a change in the absorption of the dyes, formed under the effect of the oxidizing agent, or the directly employed dyes on the keratinic fibers and thus to a greatly changed coloring result compared with the standardized carrier.

Such color differences or changed coloring results are called a "color shift" in the context of the present application. This color shift, also called dE or $\Delta E$, can be determined colorimetrically with a colorimeter with which the colors in the L*,a*,b* color space are measured, for example, with a colorimeter from the company Datacolor, Spectraflash 450 type.

The L*,a*,b* color space is understood to be the CIELAB color space. The "L" value in this case stands for the lightness of the color (black-white axis); the higher the "L" value, the lighter the color. The "a" value stands for the red-green axis of the system; the higher this value, the more the color is shifted into red. The "b" value stands for the yellow-blue axis of the system; the higher this value, the more the color is shifted into yellow.

The color shift $\Delta E$, therefore the color difference between two (hair) colors, for each of which an L*,a*,b* value combination was determined, is calculated according to following formula:

$$\Delta E = ((L_i - L_0)^2 + (a_i - a_0)^2 + (b_i - b_0)^2)^{1/2}$$

$a_0$, $b_0$, and $L_0$ are the L*, a*, and b* values for the hair strands dyed with use of the standardized carrier, whereas $a_i$, and $L_i$ are the L*, a*, and b* values that are obtained for colors with the use of care and/or active substances in the standardized carrier. The higher the value for $\Delta E$, the more pronounced the color difference or "color shift." Color differences with $\Delta E < 1$ are not perceptible by the human eye. Color differences with $\Delta E < 2$ are only visible to the trained eye. Color differences with $\Delta E > 2$ are also visible to the untrained eye.

In the worst case, the addition of an additive to a standardized carrier causes a color shift, relative to the standard carrier without additives, of $\Delta E > 2$, which therefore is also visible to the untrained eye of the consumer. To avoid having to perform complicated tests with each addition of additives to the standardized carriers with respect to the achievable hair color and optionally the fastness properties, it is therefore desirable to identify the active and care substances for the hair, the addition of which causes no or at least only a minor color shift.

The object forming the basis for the present invention therefore was to provide cosmetic agents for color modification of keratinic fibers, which include one or more selected care and active substances that cause no or only a minimal color shift.

It was now found surprisingly that the addition of at least one special nonionic silicone polymer in cosmetic agents for dyeing keratinic fibers, in particular human hair, leads to improved care, in particular to a better compatibility with a simultaneously minimal color shift of ΔE<2.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A cosmetic agent for changing the color of keratinic fibers, comprising in a cosmetically acceptable carrier at least one compound, selected from the group of oxidation dye precursors, direct dyes, and mixtures thereof; and at least one nonionic silicone polymer, including at least one structural unit of the formula (I) and at least one structural unit of the formula (II)

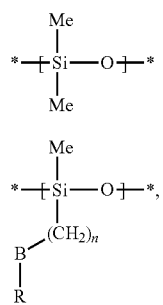

where n stands for integers from 1 to 5; B stands for a direct bond or a heteroatom from the group of O, N, or S; and R stands for a group *—(CH$_2$CH$_2$O)$_x$—H or *—(CH$_2$CHMeO)$_y$—H or *—(CH$_2$CH$_2$O)$_x$—(CH$_2$CHMeO)$_y$—H, where x and y, in each case independently of one another, stand for integers from 2 to 20.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first subject of the present invention is a cosmetic agent for color modification of keratinic fibers, comprising in a cosmetically acceptable carrier
a) at least one compound, selected from the group of oxidation dye precursors, direct dyes, and mixtures thereof,
b) at least one nonionic silicone polymer, including at least one structural unit of the formula (I) and at least one structural unit of the formula (II)

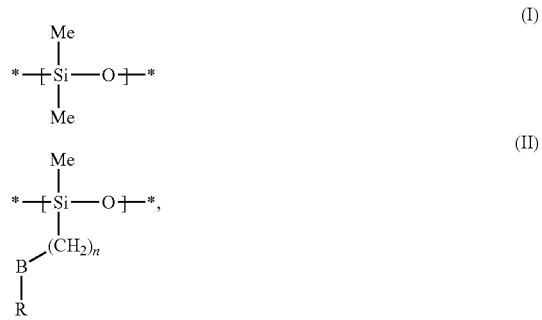

where
n stands for integers from 1 to 5,
B stands for a direct bond or a heteroatom from the group of O, N, or S, and
R stands for a group *—(CH$_2$CH$_2$O)$_x$—H or *—(CH$_2$CHMeO)$_y$—H or *—(CH$_2$CH$_2$O)$_x$—(CH$_2$CHMeO)$_y$—H,
where x and y, in each case independently of one another, stand for integers from 2 to 20.

According to the above formulas and all following formulas, a chemical bond labeled with the symbol "*" stands for a free valence of the corresponding structural fragment. A free valence in this case is understood to be the number of atomic bonds that originate from the corresponding structural fragment at the position labeled with the symbol "*." In the context of the present invention, preferably in each case an atomic bond originates from the positions, labeled with the symbol "*," of the structural fragments to other structural fragments.

The term "keratinic fibers or keratin fibers as well" according to the invention is understood to mean pelts, wool, feathers, and human hair. It is particularly preferred in the context of the present invention if the cosmetic agents are used for dyeing human hair.

Furthermore, the term "nonionic silicone polymers" in the context of the present invention is understood to mean silicone polymers that have no permanently anionic or permanently cationic groups and no anionizable or cationizable groups, such as, for example, carboxylic acid groups or amine groups.

In addition, the term "combability" in the context of the present invention is understood to mean both the combability of wet fibers and also the combability of dry fibers.

Moreover, the term "fatty alcohols" in the context of the present invention is understood to mean aliphatic, long-chain, monohydric, primary alcohols, which have unbranched hydrocarbon groups having 6 to 30 carbon atoms. The hydrocarbon groups can be saturated but also mono- or polyunsaturated.

Lastly, the term "fatty acids" in the context of the present invention is understood to mean aliphatic monocarboxylic acids with unbranched carbon atoms, which have hydrocarbon groups having 6 to 30 carbon atoms. The hydrocarbon groups can be either saturated or also mono- or polyunsaturated.

The specification of the total amount in regard to the components of the cosmetic agent in the present case, unless specified otherwise, refers to the total amount of active substance of the particular component. Furthermore, the specification of the total amount in regard to the components of the cosmetic agent, unless specified otherwise, refers to the total weight of the oxidizing agent-free cosmetic agent of the invention.

The agents of the invention include a cosmetic carrier. According to the invention, the cosmetic carrier is preferably aqueous, alcoholic, or aqueous-alcoholic. For example, creams, emulsions, gels, or surfactant-containing foaming solutions such as, for example, shampoos, foam aerosols, or other preparations, suitable for use on hair, are used in the context of the present invention.

An aqueous carrier in the context of the invention includes at least 30% by weight, particularly at least 50% by weight of water, based on the total weight of the cosmetic agent.

Aqueous-alcoholic carriers in the context of the present invention are to be understood as water-containing compositions, containing a $C_1$-$C_4$ alcohol in a total amount of 3 to 90% by weight, based on the total weight of the cosmetic agent, in particular ethanol or isopropanol.

The agents of the invention can include in addition further organic solvents such as, for example, methoxybutanol, ethyl diglycol, 1,2-propylene glycol, n-propanol, n-butanol, n-butylene glycol, glycerol, diethylene glycol monoethyl ether, and diethylene glycol mono-n-butyl ether. Preferred in this case are all water-soluble organic solvents, the solvent being contained in a total amount of 0.1 to 30% by weight, preferably of 1 to 20% by weight, in particular of 2 to 10% by weight, based on the total weight of the cosmetic agent.

The cosmetic agent of the invention includes as a first essential component a) a compound selected from the group of oxidation dye precursors (ODP), direct dyes (DD), and mixtures thereof.

In one preferred embodiment, the agents of the invention include at least one oxidation dye precursor.

Oxidation dye precursors based on their reaction behavior can be divided into two categories, so-called developer components and coupler components. Developer components can form the actual dye with themselves. They can therefore be present as the only compounds in the cosmetic agent of the invention. In one preferred embodiment, the cosmetic agents of the invention therefore include at least one oxidation dye precursor of the developer type. It can also be provided in the context of the present invention, however, that the cosmetic agents of the invention include at least one oxidation dye precursor of the coupler type. Especially good results are obtained in regard to the dyeing of keratinic fibers, if the cosmetic agents of the invention include at least one oxidation dye precursor of the developer type and at least one oxidation dye precursor of the coupler type.

The developer and coupler components are usually used in the free form. In the case of substances with amino groups, however, it can be preferred to use the salt form thereof, in particular in the form of the hydrochlorides and hydrobromides or sulfates.

Cosmetic agents are preferred according to the invention that include the developer and/or coupler components each in a total amount of 0.001 to 10% by weight, primarily of 0.01 to 8% by weight, preferably of 0.1 to 5% by weight, in particular of 0.5 to 3% by weight, based on the total weight of the cosmetic agent.

In another preferred embodiment, the cosmetic agent of the invention is therefore characterized in that it includes an oxidation dye precursor of the developer and/or coupler type in a total amount of 0.001 to 10% by weight, primarily of 0.01 to 8% by weight, preferably of 0.1 to 5% by weight, in particular of 0.5 to 3% by weight, based on the total weight of the cosmetic agent.

Suitable oxidation dye precursors of the developer type are, for example, p-phenylenediamine and the derivatives thereof. Preferred p-phenylenediamines are selected from one or more compounds of the group formed by p-phenylenediamine, p-toluylenediamine, 2-chloro-p-phenylenediamine, 2,3-dimethyl-p-phenylenediamine, 2,6-dimethyl-p-phenylenediamine, N,N-bis(2-hydroxyethyl)-p-phenylenediamine, 2-(2-hydroxyethyl)-p-phenylenediamine, 2-(1,2-dihydroxyethyl)-p-phenylenediamine, N-(2-hydroxypropyl)-p-phenylenediamine, N-(4'-aminophenyl)-p-phenylenediamine, 2-methoxymethyl-p-phenylenediamine, N-phenyl-p-phenylenediamine, 2-(2-hydroxyethyl)-p-phenylenediamine, and N-(4-amino-3-methylphenyl)-N-[3-(1H-imidazol-1-yl)propyl]amine, and the physiologically acceptable salts thereof.

It can be preferable furthermore according to the invention to use as developer component compounds that include at least two aromatic rings substituted with amino and/or hydroxyl groups. Preferred bicyclic developer components are selected from N,N'-bis(2-hydroxyethyl)-N,N'-bis(4'-aminophenyl)-1,3-diaminopropan-2-ol, N,N'-bis(4-aminophenyl)-1,4-diazacycloheptane, bis(2-hydroxy-5-aminophenyl)methane, and the physiologically acceptable salts thereof.

It can be preferred furthermore according to the invention to use a p-aminophenol derivative or one of the physiologically acceptable salts thereof as a developer component. Preferred p-aminophenols are p-aminophenol, N-methyl-p-aminophenol, 4-amino-3-methylphenol, 4-amino-2-aminomethylphenol, 4-amino-2-(1,2-dihydroxyethyl)phenol, 4-amino-2-(diethylaminomethyl)phenol, and the physiologically acceptable salts thereof.

Further, the developer component can be selected from o-aminophenol and the derivatives thereof, preferably from 2-amino-4-methylphenol, 2-amino-5-methylphenol, 2-amino-4-chlorophenol, and/or the physiologically acceptable salts thereof.

Furthermore, the developer component can be selected from heterocyclic developer components, such as pyrimidine derivatives, pyrazole derivatives, pyrazolopyrimidine derivatives, or the physiologically acceptable salts thereof. Preferred pyrimidine derivatives are 2,4,5,6-tetraaminopyrimidine, 4-hydroxy-2,5,6-triaminopyrimidine, and the physiologically acceptable salts thereof. A preferred pyrazole derivative is 4,5-diamino-1-(2-hydroxyethyl)pyrazole and the physiologically acceptable salts thereof. Pyrazolo[1,5-a]pyrimidines are preferred in particular as pyrazolopyrimidines.

Preferred oxidation dye precursors of the developer type are selected from the group formed by p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis(2-hydroxyethyl)-N,N'-bis(4-aminophenyl)-1,3-diaminopropan-2-ol, bis(2-hydroxy-5-aminophenyl) methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)

pyrazole, 2,4,5,6-tetraaminopyrimidine, 4-hydroxy-2,5,6-triaminopyrimidine, 2-hydroxy-4,5,6-triaminopyrimidine, or the physiologically acceptable salts of said compounds.

Particularly preferred developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole, and the physiologically acceptable salts thereof.

According to a further preferred embodiment of the present invention, the cosmetic agent of the invention includes as the oxidation dye precursor, apart from at least one developer component, furthermore in addition at least one coupler component. M-Phenylendiamine derivatives, naphthols, resorcinol and resorcinol derivatives, pyrazolones, and m-aminophenol derivatives are generally used as coupler components.

Coupler components preferred according to the invention are selected from (A) m-aminophenol and derivatives thereof, in particular 3-aminophenol, 5-amino-2-methylphenol, 3-amino-2-chloro-6-methylphenol, 5-amino-4-chloro-2-methylphenol, 5-(2'-hydroxyethyl)amino-2-methylphenol, and 2,4-dichloro-3-aminophenol, (B) o-aminophenol and derivatives thereof, such as 2-amino-5-ethylphenol, (C) m-diaminobenzene and derivatives thereof such as, for example, 2,4-diaminophenoxyethanol, 1,3-bis(2',4'-diaminophenoxy)propane, 1-methoxy-2-amino-4-(2'-hydroxyethylamino)benzene, 2,6-bis(2'-hydroxyethylamino)-1-methylbenzene, 2-({3-[(2-hydroxyethyl)amino]-4-methoxy-5-methylphenyl}-amino)ethanol, and 2-({3-[(2-hydroxyethyl)amino]-2-methoxy-5-methylphenyl}amino)ethanol, (D) o-diaminobenzene and derivatives thereof, (E) di- or trihydroxybenzene derivatives, in particular resorcinol, 2-chlororesorcinol, 4-chlororesorcinol, 2-methylresorcinol, and 1,2,4-trihydroxybenzene, (F) pyridine derivatives, in particular 3-amino-2-methylamino-6-methoxypyridine, 2,6-diaminopyridine, 2,6-dihydroxy-3,4-dimethylpyridine, 2-amino-3-hydroxypyridine, and 3,5-diamino-2,6-dimethoxypyridine, (G) naphthalene derivatives, such as 1-naphthol and 2-methyl-1-naphthol, (H) morpholine derivatives, such as 6-hydroxybenzomorpholine, (I) quinoxaline derivatives, (J) pyrazole derivatives, such as 1-phenyl-3-methylpyrazol-5-one, (K) indole derivatives, such as 6-hydroxyindole, (L) pyrimidine derivatives, or (M) methylenedioxybenzene derivatives, such as 1-(2'-hydroxyethyl)amino-3,4-methylenedioxybenzene, and physiologically acceptable salts thereof.

Coupler components preferred according to the invention are selected from the group, formed by 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino) ethanol, 2-({3-[(2-hydroxyethyl)amino]-2-methoxy-5-methylphenyl}amino)ethanol, 2-({3-[(2-hydroxyethyl) amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or the physiologically acceptable salts of the aforementioned compounds.

Coupler components particularly preferred according to the invention are resorcinol, 2-methylresorcinol, 5-amino-2-methylphenol, 3-aminophenol, 2-(2,4-diaminophenoxy) ethanol, 1,3-bis(2,4-diaminophenoxy)propane, 1-methoxy-2-amino-4-(2'-hydroxyethylamino)benzene, 2-amino-3-hydroxypyridine, 2,6-dihydroxy-3,4-dimethylpyridine, 1,5-dihydroxynaphthalene, 2,7-dihydroxynaphthalene, and 1-naphthol, and the physiologically acceptable salts thereof.

In a particularly preferred embodiment of the present invention, the cosmetic agents of the invention are characterized in that they include as the oxidation dye precursor at least one developer component, selected from the group comprising p-phenylenediamine, p-toluylendiamine, N,N-bis(2-hydroxyethyl)amino-p-phenylenediamine, 1,3-bis[(2-hydroxyethyl-4'-aminophenyl)amino]propan-2-ol, 1,10-bis (2',5'-diaminophenyl)-1,4,7,10-tetraoxadecane, 4-aminophenol, 4-amino-3-methylphenol, bis(5-amino-2-hydroxyphenyl)methane, 2,4,5,6-tetraaminopyrimidine, 2-hydroxy-4,5,6-triaminopyrimidine, 4,5-diamino-1-(2-hydroxyethyl)pyrazole, the physiologically acceptable salts thereof and mixtures thereof, and at least one coupler component, selected from the group comprising resorcinol, 2-methylresorcinol, 5-methylresorcinol, 2,5-dimethylresorcinol, 4-chlororesorcinol, resorcinol monomethyl ether, 5-aminophenol, 5-amino-2-methylphenol, 5-(2-hydroxyethyl)amino-2-methylphenol, 3-amino-4-chloro-2-methylphenol, 3-amino-2-chloro-6-methylphenol, 3-amino-2,4-dichlorphenol, 2,4-diaminophenoxyethanol, 2-amino-4-(2'-hydroxyethyl)aminoanisole sulfate, 1,3-bis(2,4-diaminophenoxy)propane, 2-amino-3-hydroxypyridine, 2-methylamino-3-amino-6-methoxypyridine, 2,6-cihydroxy-3,4-dimethylpyridine, 3,5-diamino-2,6-dimethoxypyridine, 1-naphthol, 2-methyl-1-naphthol, 1,5-dihydroxynaphthalene, 2,7-dihydroxynaphthalene, 1-phenyl-3-methylpyrazol-5-one, 2,6-bis[(2'-hydroxyethyl)amino] toluene, 4-hydroxyindole, 6-hydroxyindole, 6-hydroxybenzomorpholine, and the physiologically acceptable salts thereof and mixtures thereof.

To obtain a balanced and subtle nuance formation, it can also be provided in the context of the present invention that the cosmetic agents of the invention in addition include at least one direct dye. Direct dyes are dyes that are directly absorbed onto the hair and do not require any oxidative process to develop the color. Direct dyes are usually nitrophenylenediamines, nitroaminophenols, azo dyes, anthraquinones, or indophenols.

Direct dyes can be divided into anionic, cationic, and nonionic direct dyes.

Preferred anionic direct dyes are the compounds known under the names: Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, and tetrabromophenol blue. Preferred cationic direct dyes are cationic triphenylmethane dyes, such as Basic Blue 7, Basic Blue 26, Basic Violet 2, and Basic Violet 14, and aromatic systems, which are substituted with a quaternary nitrogen group, such as Basic Yellow 57, Basic Red 76, Basic Blue 99, Basic Brown 16, and Basic Brown 17 and HC Blue 16, as well as Basic Yellow 87, Basic Orange 31, and Basic Red 51. Preferred nonionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydro-quinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Furthermore, naturally occurring dyes as well can be used as direct dyes, as are found, for example, in henna red, henna neutral, henna black, chamomile blossoms, sandalwood, black tea, walnut, buckthorn bark, sage, logwood, madder root, catechu, and alkanna root.

Preferably the cosmetic agent of the invention includes the direct dyes in a total amount of 0.001 to 10% by weight, primarily of 0.01 to 8% by weight, preferably of 0.1 to 5% by weight, in particular of 0.5 to 3% by weight, based on the total weight of the cosmetic agent.

The cosmetic agents of the invention include at least one special nonionic silicone polymer as the second essential component d). The addition of said silicone polymer results in improved care, in particular wet combability, but without causing a color shift visible to the untrained human eye; i.e., the color change ΔE caused by the addition of special nonionic silicone polymers is less than 2.

According to a preferred embodiment of the present invention, in the structural unit of the formula (II), n stands for the integer 2 or 3 and B for the heteroatom O.

Especially good results in the context of the present invention are obtained, if the group R in the structural unit of the formula (II) stands for a group *—(CH$_2$CH$_2$O)$_x$—H, where x stands for integers from 2 to 20, primarily from 3 to 15, preferably from 4 to 10, in particular from 5 to 9.

Particularly preferable according to the invention, the cosmetic agent includes at least one nonionic silicone polymer of the formula (III)

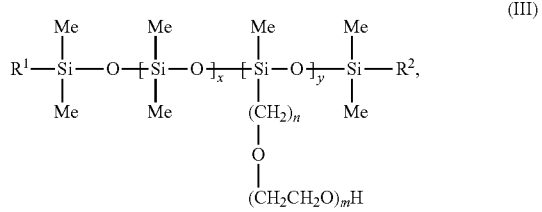

(III)

where
R$^1$ and R$^2$, in each case independently of one another, stand for a methyl group or a hydroxyl group, x and y, in each case independently of one another, stand for integers from 1 to 2000, primarily from 1 to 1800, preferably from 1 to 1500, in particular from 1 to 1000,
n stands for integers from 1 to 5, primarily from 1 to 4, preferably from 1 to 3, in particular 2 or 3, and
m stands for integers from 2 to 20, primarily from 3 to 15, preferably from 4 to 10, in particular from 5 to 9. The use of these special nonionic silicone polymers results in increased care of the keratinic fibers after the color change and simultaneously does not lead to a color shift of the coloring result visible to the untrained human eye. The aforementioned silicone polymers can therefore be used in any standardized carriers, without an adjustment of the oxidation dye precursors and optionally the direct dyes being necessary to compensate for the color shift caused by the addition.

Preferably, the at least one nonionic silicone polymer b) has an average molecular weight M$_w$ of 350 to 200,000 Da, primarily of 500 to 180,000 Da, preferably of 1000 to 150,000 Da, in particular of 3000 to 100,000 Da. Special nonionic silicone polymers, which have the aforementioned average molecular weight M$_w$, result in an especially high care for keratinic fibers after the color change with a simultaneously minimal color shift of ΔE<2 not visible to the untrained human eye. The average molecular weight M$_w$ can be determined, for example, by gel permeation chromatography (GPC) (Liu X. M. et al.; "*Comparative studies of poly(dimethylsiloxanes) using automated GPC-MALDI-TOF MS and on-line GPC-ESI-TOF MS*"; J. Am. Soc. Mass. Spectrom., 2003, 14, pages 195 to 202).

The at least one nonionic silicone polymer b) is contained in the cosmetic agents of the invention in a total amount of 0.00001 to 7.0% by weight, primarily of 0.00005 to 5.0% by weight, preferably of 0.0005 to 3.5% by weight, more preferably of 0.001 to 1.0% by weight, in particular of 0.005 to 0.5% by weight, based on the total weight of the cosmetic agent. The use of the aforementioned total amount of the special nonionic silicone polymer leads to increased care of the keratinic fibers, however, without influencing the coloring result in the form of a visible color shift.

It emerged that an addition of polyoxyethylene (20) sorbitan monolaurate can stabilize the at least one nonionic silicone polymer, in particular the nonionic silicone polymer of the formula (III), in the cosmetic agents of the invention, so that the care effects are enhanced further. Cosmetic agents preferred according to the invention therefore include in addition polyoxyethylene (20) sorbitan monolaurate in a total amount of 0.003 to 1.5% by weight, primarily of 0.006 to 1.1% by weight, preferably of 0.009 to 0.8% by weight, more preferably of 0.01 to 0.5% by weight, in particular of 0.015 to 0.3% by weight, based on the total weight of the cosmetic agent.

The at least one nonionic silicone polymer, in particular the nonionic silicone polymer of the formula (III), can be stabilized further by the addition of polyoxyethylene (7) lauryl ether. It is therefore preferred in the context of the present invention, if the cosmetic agents of the invention include in addition polyoxyethylene (7) lauryl ether in a total amount of 0.01 to 6% by weight, primarily of 0.02 to 4.5% by weight, preferably of 0.03 to 3% by weight, more preferably of 0.04 to 2.1% by weight, in particular of 0.05 to 1.5% by weight, based on the total weight of the cosmetic agent.

The cosmetic agents of the invention can include other active substances and additives. It is therefore preferred in the context of the present invention, if the cosmetic agent in addition includes at least one further compound, selected from the group comprising (i) thickeners; (ii) linear or branched, saturated or unsaturated alcohols having 8 to 20 carbon atoms; (iii) surfactants, in particular amphoteric surfactants; (iv) alkalizing agents; (v) oils; as well as (vi) mixtures thereof.

Preferably, the cosmetic agents of the invention are formulated as flowable preparations. In this case, the cosmetic agents should be formulated so that, on the one hand, they can be applied and distributed well at the application site but, on the other, are sufficiently viscous, so that they remain at the site of action during the contact time and do not run.

It has proven advantageous, therefore, according to the invention, if the cosmetic agents of the invention include at least one thickener from the group of (i) anionic, synthetic polymers; (ii) cationic, synthetic polymers; (iii) naturally occurring thickeners, such as nonionic guar gums, scleroglucan gums or xanthan gums, gum arabic, gum ghatti, karaya gum, tragacanth gum, carrageenan gum, agar-agar, locust bean flour, pectins, alginates, starch fractions and derivatives such as amylose, amylopectin, and dextrins, as well as cellulose derivatives such as, for example, methylcellulose, carboxyalkyl celluloses, and hydroxyalkyl celluloses; (iv) nonionic, synthetic polymers, such as polyvinyl alcohol or polyvinylpyrrolidinone; (v) inorganic thickeners, in particular phyllosilicates such as, for example, bentonite, particularly smectites, such as montmorillonite or hectorite; as well as (vi) mixtures thereof, in a total amount of 0.0005 to 5.0% by weight, primarily of 0.001 to 3.0% by weight, preferably of 0.005 to 1.0% by weight, in particular of 0.008 to 0.01% by weight, based on the total weight of the cosmetic agent.

It has emerged as advantageous in the context of the present invention, if at least one naturally occurring thickener, in particular xanthan gum and salts thereof, is contained as a thickener in a total amount of 0.0005 to 5.0% by weight, primarily of 0.001 to 1.0% by weight, preferably of 0.005 to 0.5% by weight, in particular of 0.01 to 0.1% by weight, based on the total weight of the cosmetic agent.

It can be preferred in the context of the present invention, if the linear or branched, saturated or unsaturated alcohol having 8 to 20 carbon atoms is selected from the group comprising myristyl alcohol (1-tetradecanol), stearyl alcohol (1-octadecanol), cetearyl alcohol, 2-octyldodecanol, arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), primarily 2-octyldodecanol and/or cetearyl alcohol, and is contained in a total amount of 1.0 to 35% by weight, primarily of 5.0 to 30% by weight, preferably of 10 to 25% by weight, in particular of 12 to 20% by weight, based on the total weight of the cosmetic agent.

Preferably the cosmetic agents of the invention can contain, furthermore, at least one partial ester from a polyol having 2 to 6 carbon atoms and linear saturated carboxylic acids having 12 to 30, in particular 14 to 22 carbon atoms, wherein the partial ester can be hydroxylated, in a total amount of 0.5 to 10% by weight, in particular of 3.0 to 8.0% by weight, based on the total weight of the cosmetic agent. Such partial esters are in particular the mono- and diesters of glycerol or the monoesters of propylene glycol or the mono- and diesters of ethylene glycol or the mono-, di-, tri-, and tetraesters of pentaerythritol in each case with linear saturated $C_{12}$-$C_{30}$ carboxylic acids, which may be hydroxylated, in particular those with palmitic and stearic acid, the sorbitan mono-, di-, or triesters of linear saturated $C_{12}$-$C_{30}$ carboxylic acids, which may be hydroxylated, in particular those of myristic acid, palmitic acid, stearic acid, or of mixtures of these fatty acids and the methyl glucose mono- and diesters of linear saturated $C_{12}$-$C_{30}$ carboxylic acids, which may be hydroxylated.

In the context of the present invention, it can be provided that the cosmetic agents of the invention include at least one polyol partial ester, selected from glycerol monostearate, glycerol monopalmitate, glycerol distearate, glycerol dipalmitate, ethylene glycol monostearate, ethylene glycol monopalmitate, ethylene glycol distearate, ethylene glycol dipalmitate, and mixtures thereof, in particular mixtures of glycerol monostearate, glycerol monopalmitate, glycerol distearate, and glycerol dipalmitate in a total amount of 0.5 to 10% by weight, in particular of 3.0 to 8.0% by weight, based on the total weight of the cosmetic agent.

The use of the aforementioned alcohols, partial esters, and poly partial esters in the cosmetic agents of the invention can be particularly preferred when the cosmetic agents of the invention are present in the form of a cream-like oil-in-water emulsion.

It can be provided according to the invention, furthermore, that the cosmetic agents according to the invention include at least one surfactant. Surfactants in the context of the present invention are amphiphilic (bifunctional) compounds, which consist of at least one hydrophobic and at least one hydrophilic moiety. A basic property of surfactants and emulsifiers is the oriented absorption on interfaces and the aggregation to form micelles and the formation of lyotrophic phases.

According to one preferred embodiment of the present invention, the cosmetic agents of the invention include at least one amphoteric surfactant in a total amount of 0.1 to 5.0% by weight, in particular of 0.2 to 2.0% by weight, based on the total weight of the cosmetic agent. Surface-active compounds that have at least one quaternary ammonium group and at least one $—COO^{(-)}$ or $—SO3^{(-)}$ group can be called amphoteric or zwitterionic surfactants.

The compounds listed below are particularly preferred as amphoteric surfactants in the context of the present invention:

alkyl betaines having 8 to 20 carbon atoms in the alkyl group,
  amidopropyl betaines having 8 to 20 carbon atoms in the acyl group,
  sulfobetaines having 8 to 20 carbon atoms in the acyl group, and
  amphoacetates or amphodiacetates having 8 to 20 carbon atoms in the acyl group.

In a particularly preferred embodiment, the cosmetic agents of the invention include as a surfactant at least one amphoteric surfactant, selected from amidopropyl betaines having 9 to 13 carbon atoms in the acyl group, in a total amount of 0.1 to 5.0% by weight, in particular of 0.2 to 2.0% by weight, based on the total weight of the cosmetic agent.

It can be provided, furthermore, that the cosmetic agents of the invention include at least one ethoxylated nonionic surfactant in a total amount of 0.5 to 6.0% by weight, in particular of 1.0 to 4.0% by weight, based on the total weight of the cosmetic agent. In this case, it has emerged as especially advantageous, if the ethoxylated nonionic surfactant has an HLB value above 10, preferably above 13. It is necessary to this end that the nonionic surfactant has a sufficiently high ethoxylation degree. In this regard, the cosmetic agent of the invention therefore includes as the ethoxylated nonionic surfactant at least one ethoxylated surfactant with at least 12 ethylene oxide units. Apart from the suitably ethoxylated fatty alcohols, in particular lauryl alcohol, myristyl alcohol, cetyl alcohol, stearyl alcohol, arachyl alcohol, and behenyl alcohol, in particular according to the invention the adducts of 20 to 60 mol of ethylene oxide to castor oil and hydrogenated castor oil are especially suitable. The at least one ethoxylated nonionic surfactant is preferably selected from surfactants with the INCI name Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil, and PEG-60 Hydrogenated Castor Oil, and mixtures of these substances, selected particularly preferably from Ceteth-20, Steareth-20, Ceteareth-20, Ceteth-30, Steareth-30, and Ceteareth-30.

Cosmetic agents in the context of the present invention normally have a basic pH, in particular between pH 8.0 and pH 12. These pH values are necessary to assure an opening of the outer cuticle layer (cuticle) and to enable penetration of the oxidation dye precursors and/or the oxidizing agent into the hair.

The aforementioned pH can be established preferably with the use of an alkalizing agent. In the context of the present invention, the alkalizing agent is selected from the group of (i) inorganic alkalizing agents; (ii) organic alkalizing agents; and (iii) mixtures thereof, and in a total amount of 1.5 to 9.5% by weight, primarily of 2.5 to 8.5% by weight, preferably of 3.0 to 8.0% by weight, in particular of 3.5 to 7.5% by weight, based on the total weight of the cosmetic agent.

Preferred inorganic alkalizing agents are selected from the group formed by ammonia or ammonium hydroxide, therefore aqueous solutions of ammonia, sodium hydroxide, potassium hydroxide, calcium hydroxide, barium hydroxide, sodium phosphate, potassium phosphate, sodium silicate, potassium silicate, sodium carbonate, and potassium carbonate, and mixtures thereof. Ammonia or ammonium hydroxide is a particularly preferred alkalizing agent. Ammonia is particularly preferred in a total amount of 0.1 to 20% by weight, preferably of 0.5 to 10% by weight, in particular of 1.0 to 7.0% by weight, based on the total weight of the cosmetic agent.

Preferred organic alkalizing agents are selected from at least one alkanolamine. Alkanolamines preferred according to the invention are selected from alkanolamines from primary, secondary, or tertiary amines with a $C_2$-$C_6$ alkyl parent structure, bearing at least one hydroxyl group. Particularly preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methylpropanol, 2-amino-2-methylbutanol, 3-amino-2-methylpropan-1-ol, 1-amino-2-methylpropan-2-ol, 3-aminopropane-1,2-diol, 2-amino-2-methylpropane-1,3-diol, 2-amino-2-ethyl-1,3-propanediol, N,N-dimethylethanolamine, triethanolamine, diethanolamine, and triisopropanolamine. Alkanolamines very especially preferred according to the invention are selected from the group comprising 2-aminoethan-1-ol (monoethanolamine), 2-amino-2-methylpropan-1-ol, 2-amino-2-methylpropane-1,3-diol, and triethanolamine. Particularly preferred cosmetic agents of the invention include a mixture of monoethanolamine and 2-amino-2-methylpropan-1-ol. Preferably the at least one alkanolamine is contained in a total amount of 0.05 to 15% by weight, preferably of 0.5 to 10% by weight, and in particular of 3.5 to 7.5% by weight, based on the total weight of the cosmetic agent.

Other organic alkalizing agents preferred according to the invention are selected from basic amino acids, particularly preferably selected from the group formed by L-arginine, D-arginine, D/L-arginine, L-lysine, D-lysine, D/L-lysine, and mixtures thereof. Basic amino acids particularly preferred according to the invention are selected from L-arginine, D-arginine, and D/L-arginine. Preferred cosmetic agents of the invention include at least one alkalizing agent, different from alkanolamines and ammonia, in a total amount of 0.05 to 5.0% by weight, in particular of 0.5 to 3.0% by weight, based on the total weight of the cosmetic agent.

In a particularly preferred embodiment, the cosmetic agents of the invention include as alkalizing agents a mixture of at least two alkanolamines different from one another, in particular of monoethanolamine and 2-amino-2-methylpropan-1-ol, in a total amount of 0.05 to 15% by weight, preferably of 0.5 to 10% by weight, in particular of 3.5 to 7.5% by weight, based on the total weight of the cosmetic agent.

Preferably, the pH of the cosmetic agents of the invention, measured at 22° C., is 8 to 13, primarily 9.5 to 12, preferably 10 to 11.5, in particular 10.5 to 11.

In the context of the present invention, it can be preferred furthermore if the cosmetic agents of the invention include at least one oil, selected from the group comprising sunflower oil, corn oil, soy oil, pumpkin seed oil, grape seed oil, sesame oil, hazelnut oil, apricot kernel oil, macadamia nut oil, arara oil, castor oil, avocado oil, and mixtures thereof, in a total amount of 0.1 to 10% by weight, preferably of 0.2 to 5.0% by weight, and in particular of 0.5 to 2.0% by weight, based on the total weight of the cosmetic agent. The care effect of the nonionic silicone polymers can be increased further by the use of an aforementioned oil.

Particularly preferably, the cosmetic agents of the invention include grape seed oil in a total amount of 0.1 to 10% by weight, preferably of 0.2 to 5.0% by weight, in particular of 0.5 to 2.0% by weight, based on the total weight of the cosmetic agent.

According to a particularly preferred embodiment of the present invention, the cosmetic agents present as an oil-in-water emulsion contain, based on the total weight of the cosmetic agents,
  cetearyl alcohol in a total amount of 2.0 to 20% by weight, in particular of 5.0 to 12% by weight, further
  mixtures of glycerol monostereate, glycerol monopalmitate, glycerol distearate, and glycerol dipalmitate in a total amount of 0.5 to 10% by weight, preferably 3.0 to 8.0% by weight, further
  at least one amphoteric surfactant, selected from amidopropyl betaines having 9 to 13 carbon atoms in the acyl group, in a total amount of 0.1 to 5.0% by weight, in particular of 0.2 to 2.0% by weight, further
  a mixture of at least two alkanolamines different from one another, in particular of monoethanolamine and 2-amino-2-methylpropan-1-ol, in a total amount of 0.05 to 15% by weight, preferably of 0.5 to 10% by weight, and in particular of 3.5 to 7.5% by weight, further
  grape seed oil in a total amount of 0.1 to 10% by weight, preferably of 0.2 to 5.0% by weight, in particular of 0.5 to 2.0% by weight.

Oxidative dye compositions can also be prepared immediately before use from two or more separately packaged compositions. This lends itself in particular for separating incompatible ingredients in order to prevent a premature reaction. Separation into multi-component systems is preferred particularly when incompatibilities of the ingredients are a possibility or a risk. The oxidative dye composition in these cases is prepared by the consumer immediately before use by mixing the components. In the context of the present invention, this procedure in the case of oxidative dyes, in which the cosmetic agent of the invention is present initially separated from an oxidizing agent preparation 47 at least one oxidizing agent, is particularly preferred.

A further subject of the present invention therefore is a packaging unit (kit of parts), comprising, produced separately from one another,
a) at least one container (C1), containing a cosmetic agent of the invention, and
b) at least one container (C2), containing an oxidizing agent preparation, which in a cosmetically acceptable carrier includes at least one oxidizing agent in a total amount of 0.5 to 7.0% by weight, preferably of 1.0 to 7.0% by weight, in particular of 3.0 to 7.0% by weight, based on the total weight of the oxidizing agent preparation, and at least one acid.

The use of the at least one nonionic silicone polymer in combination with specific amounts of oxidizing agents during use of the aforesaid packaging unit for dyeing keratinic fibers surprisingly results in increased care, in particular in an increased wet combability, but without a color shift of ΔE>2, perceptible with the untrained human eye, occurring due to the addition of the nonionic silicone polymer.

The term "container" in the context of the present invention is understood to mean a wrapping, which is present in the form of an optionally reclosable bottle, tube, a box, a small packet, a sachet, or similar wrappings. No limits are imposed on the wrapping material according to the invention. Preferably, however, these are wrappings made of glass or plastic.

The oxidizing agents in the context of the present invention are different from atmospheric oxygen. Hydrogen peroxide and the solid adducts thereof to organic and inorganic compounds can be used as oxidizing agents. Suitable solid adducts according to the invention are in particular the adducts to urea, melamine, polyvinylpyrrolidinone, and sodium borate. Hydrogen peroxide and/or one of its solid adducts to organic or inorganic compounds are particularly preferred as oxidizing agents. Preferably according to the invention, the oxidizing agent is therefore selected from the group of persulfates, chlorites, hydrogen peroxide, and adducts of hydrogen peroxide to urea, melamine, and sodium borate, in particular hydrogen peroxide.

A particularly preferred embodiment of the present invention is therefore characterized in that hydrogen peroxide is contained as the oxidizing agent in a total amount of 0.5 to 7.0% by weight, preferably of 1.0 to 7.0% by weight, and in particular of 3.0 to 7.0% by weight, based on the total weight of the oxidizing agent preparation. The calculation of the total amount in this case refers to 100% 14202.

The oxidizing agent preparations furthermore can include water in a total amount of 40 to 98% by weight, in particular of 65 to 85% by weight, based on the total weight of the oxidizing agent preparation.

According to a preferred embodiment of the present invention, the oxidizing agent preparations include further at least one linear saturated alkanol having 12 to 30 carbon atoms, in particular having 16 to 22 carbon atoms, in a total amount of 0.1 to 10% by weight, primarily of 0.5 to 5.0% by weight, in particular of 1.0 to 4.0% by weight, based on the total weight of the oxidizing agent preparation. Preferred in particular are cetyl alcohol, stearyl alcohol, arachidyl alcohol, behenyl alcohol, and lanolin alcohol or mixtures of said alcohols, as they are obtainable in the large-scale hydrogenation of plant and animal fatty acids, and mixtures of said alkanols. The cetearyl alcohol mixture is particularly preferred.

In a further preferred embodiment of the present invention, the oxidizing agent preparations include at least one ethoxylated nonionic surfactant, which is selected preferably from surfactants with the INCI name: Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil, and PEG-60 Hydrogenated Castor Oil and mixtures of said substances, selected particularly preferably from Ceteth-20, Steareth-20, Ceteareth-20, Ceteth-30, Steareth-30, and Ceteareth-30, in a total amount of 0.1 to 10% by weight, preferably of 0.5 to 5.0% by weight, in particular of 1 to 4.0% by weight based on the total weight of the oxidizing agent preparation.

In the context of the present invention, it can also be provided in addition that the oxidizing agent preparations include at least one ester from a carboxylic acid having 10 to 20 carbon atoms and a linear or branched alcohol having 1 to 5 carbon atoms, in particular isopropyl myristate, in a total amount of 3.0 to 25% by weight, primarily of 5.0 to 20% by weight, in particular of 8.0 to 15% by weight, based on the total weight of the oxidizing agent preparation.

According to a particularly preferred embodiment of the present invention, the oxidizing agent preparations contain, based on the total weight of the oxidizing agent preparations,
 at least one linear saturated alkanol having 12 to 30 carbon atoms in a total amount of 0.1 to 10% by weight, preferably of 0.5 to 5.0% by weight, in particular of 1.0 to 4.0% by weight, further
 at least one ethoxylated nonionic surfactant, which is selected preferably from surfactants with the INCI name: Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil, and PEG-60 Hydrogenated Castor Oil and mixtures of said substances, selected particularly preferably from Ceteth-20, Steareth-20, Ceteareth-20, Ceteth-30, Steareth-30, and Ceteareth-30, in a total amount of 0.1 to 10% by weight, preferably of 0.5 to 5.0% by weight, in particular of 1.0 to 4.0% by weight, and
 at least one ester from a carboxylic acid having 10 to 20 carbon atoms and a linear or branched alcohol having 1 to 5 carbon atoms, preferably isopropyl myristate, in a total amount of 3.0 to 25% by weight, preferably of 5.0 to 20% by weight, in particular of 8.0 to 15% by weight.

The oxidizing agent preparations of the invention furthermore include at least one acid. Preferred acids are selected from dipicolinic acid, edible acids such as, for example, citric acid, acetic acid, malic acid, lactic acid, and tartaric acid, dilute mineral acids such as hydrochloric acid, phosphoric acid, pyrophosphoric acid, and sulfuric acid, and mixtures thereof. The oxidizing agent preparations preferably have a pH in the range of 2 to 5, in particular of 3 to 4.

To prepare oxidative dye compositions from the packaging unit (kit of parts) of the invention, cosmetic agents of the invention in container C1 are mixed with the oxidizing agent preparation in container C2 or vice versa.

It can be especially advantageous according to the invention, further, if the packaging unit includes at least one further hair treatment agent in an additional container, in particular a conditioning agent preparation. Said conditioning agent preparation advantageously includes at least one conditioning agent, selected from the group of cationic polymers, silicone derivatives, and oils. Moreover, the packaging unit can comprise application aids, such as combs, brushes, dye brushes, or small brushes, personal protective clothing, in particular disposable gloves, and optionally instructions for use. A dye brush is understood to be a broad brush which has a point at the handle end, which permits and simplifies the separation of fiber bundles or strands from the total amount of fibers.

The statements made about the cosmetic agents of the invention apply mutatis mutandis to the cosmetic agent of the invention in container C1 and the oxidizing agent preparation in container C2.

A further subject of the present invention is a method for dyeing keratinic fibers with increased care with a simultaneously minimized color shift, wherein the method comprises the following process steps:
a) providing a cosmetic agent of the invention (M1),
b) providing an oxidizing agent preparation (M2), containing in a cosmetically acceptable carrier at least one oxidizing agent and at least one acid,
c) mixing the cosmetic agent (M1) with the oxidizing agent preparation (M2),
d) applying the mixture obtained in step c) to the keratinic fibers and leaving said mixture on the keratinic fibers for a time period of 10 to 60 minutes, preferably of 20 to 45 minutes, at room temperature and/or at least 30° C.
e) rinsing the keratinic fibers with water and/or a cleansing composition for 1 to 5 minutes, and
f) optionally applying an aftertreatment agent to the keratinic fibers and rinsing it off after a time period of 1 to 10 minutes.

The method of the invention for dyeing keratinic fibers with use of a special nonionic silicone polymer results in improved care of the dyed keratinic fibers, without however an undesirable color shift of ΔE>2, visible to the untrained human eye, resulting due to the addition of the nonionic silicone polymer.

Room temperature in the context of the present invention is understood to be the ambient temperature. The effect of the coloring and/or lightening preparation can be intensified by an external heat supply, for example, by means of a heating hood. The preferred contact time of the coloring and/or lightening preparation on the keratinic fiber is 10 to 60 minutes, preferably 20 to 45 minutes. After the contact time ends, the remaining dyeing agent is washed out of the keratinic fibers with the aid of a cleansing preparation, which preferably includes at least one cationic and/or anionic and/or nonionic surfactant, and/or water. Optionally, the process is repeated with a further agent. After the washing out, the keratinic fibers are optionally rinsed with an aftertreatment agent, for example, a conditioning agent, and dried with a towel or a hot air dryer. The application of the dye preparation usually occurs by hand by the user. Preferably, in this case, personal protective clothing is worn, in particular suitable protective gloves, for example, made of plastic or latex for a one-time use (disposable gloves), and optionally an apron. It is also possible, however, to apply the dyeing agents to the keratinic fibers with an application aid.

The statements made about the cosmetic agents of the invention and the packaging unit of the invention apply mutatis mutandis to cosmetic agent M1 of the invention, oxidizing agent preparation M2, and other preferred embodiments of the method of the invention.

Lastly, a further subject of the present invention is the use of a cosmetic agent of the invention or a packaging unit (kit of parts) of the invention to increase the care of keratinic fibers while simultaneously minimizing the color shift. The use of a special nonionic silicone polymer results in increased care of dyed keratinic fibers, without the addition of said care substance leading to an undesirable color shift of ΔE>2 visible to the untrained human eye.

The statements made about the cosmetic agents of the invention and the packaging unit of the invention apply mutatis mutandis to other preferred embodiments of the use of the invention.

The following examples are intended to illustrate the preferred embodiments of the invention, however, without restricting them.

EXAMPLES

1. Formulations

Compositions of the employed cosmetic agents (oil-in-water emulsions, all amounts given in % by weight). The nonionic silicone polymer used in the following formulations is preferably a silicone polymer of the formula (III) with n=2 or 3, m=5 to 9, and an average molecular weight $M_w$ of 3000 to 100,000 Da.

| Raw material | V1 | E1* | E2* |
|---|---|---|---|
| Xanthan gum | 0.05 | 0.05 | 0.05 |
| 2-Octyldodecanol | 2.3 | 2.3 | 2.3 |
| Lanette N [a)] | 14 | 14 | 14 |
| Cetearyl alcohol | 3.9 | 3.9 | 3.9 |
| Glycerol monostearate | 6.0 | 6.0 | 6.0 |
| Glycerol 99.5% | 2.0 | 2.0 | 2.0 |
| Cocamidopropyl betaine, 40% | 2.0 | 2.0 | 2.0 |
| Monoethanolamine | 4.5 | 4.5 | 4.5 |
| 2-Amino-2-methylpropanol | 0.10 | 0.10 | 0.10 |
| Sodium sulfite, anhydrous | 0.15 | 0.15 | 0.15 |
| Caramel syrup, 75% | 0.10 | 0.10 | 0.10 |
| Grape seed oil | 1.0 | 1.0 | 1.0 |
| p-Toluylenediamine sulfate | 0.032 | 0.032 | 0.032 |
| 4-Amino-3-methylphenol | 0.32 | 0.32 | 0.32 |
| Resorcinol | 0.037 | 0.037 | 0.037 |
| 1-Naphthol | 0.092 | 0.092 | 0.092 |
| p-Amino-o-cresol | 0.21 | 0.21 | 0.21 |
| 2-Amino-6-chloro-4-nitrophenol | 0.24 | 0.24 | 0.24 |
| Nonionic silicone polymer ** | — | 0.25 | 0.5 |
| Water, demineralized | To 100.00 | To 100.00 | To 100.00 |

*according to the invention
** active substance
[a)] INCI name: Cetearyl alcohol, Sodium cetearyl sulfate (BASF)

The fat base was melted together at 80° C. and dispersed with a portion of the water amount. The remaining formulation components were then incorporated in sequence while stirring. The mixture was then made up with water to 100% by weight and the formulation was stirred until cold. Formulation V1 is a comparison formulation, not according to the invention, without the nonionic silicone polymer. Formulations E1 and E2 are examples of the invention.

Oxidizing agent preparation O1 (all amounts given in % by weight)

| Raw material | O1 |
|---|---|
| Disodium pyrophosphate | 0.10 |
| Dipicolinic acid | 0.10 |
| Potassium hydroxide 50% | 0.22 |
| 1-Hydroxyethane-1,1-diphosphonic acid 60% | 0.25 |
| Emulgade F [b)] | 4.0 |
| Cetearyl alcohol | 0.5 |
| Ceteareth-20 | 0.5 |

-continued

| Raw material | O1 |
| --- | --- |
| Beeswax | 0.3 |
| Isopropyl myristate | 10 |
| Hydrogen peroxide 50% | 11 |
| Water, demineralized | To 100 |

[b] INCI name: Cetearyl alcohol, PEG-40 Castor oil, Sodium cetearyl sulfate (BASF)

2. Small Color Shift Due to the Addition of the Nonionic Silicone Polymer

To prepare the oxidative dyeing agents for determining the color shift, the cosmetic agents V1 as well as E1 and E2 were mixed in the weight ratio of 1:1 with the above oxidizing agent preparation O1.

The oxidative dyeing agents prepared in this way were each applied in a defined amount (4 g of the oxidative dyeing agent per 1 g of yak hair) to yak hair strands (12 strands each per oxidative dyeing agent) and remained on the hair strands for a contact time of 30 minutes at 32° C. Next, the remaining agents were each rinsed out of the hair strands for 2 minutes with lukewarm water; the strands were first dried with a towel and then blown dry.

All strands were measured with a colorimeter from the company Datacolor, Spectraflash 450 type. The ΔE values used for evaluating the color shift result from the L*a*b color values measured for each strand as follows:

$$\Delta E = ((L_i - L_0)^2 + (a_i - a_0)^2 + (b_i - b_0)^2)^{1/2}$$

$a_0$, $b_0$, and $L_0$ each are hereby averages of measured color values determined from 12 measurements of the yak hair strands dyed during use of the standardized carrier. $a_i$, $b_i$, and $L_i$ each stand for averages of measured color values, which were obtained for dyed yak hair strands with addition of the special nonionic silicone polymer to the standardized carrier.

The higher the value for ΔE, the more pronounced the color difference or "color shift." Color differences with ΔE<1 are not perceptible by the human eye. Color differences with ΔE<2 are visible to the trained eye. Color differences with ΔE>2 are also visible to the untrained eye. The ΔE values for the colors with use of the cosmetic agents E1 and E2 are presented in Table 1. The colors with the cosmetic agents E1 and E2 of the invention, which include at least one special nonionic silicone in a total amount of 0.25% by weight or 0.5% by weight, have only a minor color shift of ΔE<2, which are not visible to the untrained eye. The color shift, caused by the nonionic silicone polymer, in this case is the smaller, the lower the employed amount of the nonionic silicone polymer.

| Oxidative dyeing agents | ΔE |
| --- | --- |
| E1 + O1 (1:1) | 1.085 |
| E2 + O1 (1:1) | 1.305 |

3. Improved Care

To prepare the oxidative dyeing agents for determining the care, the cosmetic agents V1 and E2 were each mixed in the weight ratio of 1:1 with the above oxidizing agent preparation 01.

12 strands of natural light-brown European hair (IHIP (New York), lot #03/2012, N104, length 15 cm, weight 1 g) were washed with an aqueous sodium lauryl ether sulfate solution (3% active substance content in the solution). The strands were dried in air and stored for 24 hours at 25° C. and 25% relative humidity. After soaking of these strands for 5 minutes in water, their wet combability was determined (reference value).

For the dyeing, 12 strands in each case of natural European hair (IHIP (New York), lot #03/2012, N104, length 15 cm, weight 1 g) per oxidative dyeing agent were used. To this end, 4 g in each case of the oxidative dyeing agents prepared under Point 2 was applied per 1 g of hair strands. After the strands were dyed for 30 minutes at 32° C., they were rinsed for 2 minutes with water and dried in air.

The wet combability was measured as follows:

Before the measurement, each strand was moistened for 2 seconds with water while being combed with a hard rubber comb with fine teeth (company Hercules Sagemann, Hamburg, Germany). After 3 combing operations were carried out, the combing force during another 10 combing operations was measured, the particular hair strand being slowly rotated during the combing operation. The obtained measured values are compared with use of the following statistical tests incorporated in the software Statistica 10.0 (StatSoft Inc., USA):

Shapiro-Wilks test (test for normal distribution)
Grubbs outlier test
Bartlett test (test for homoscedasticity of variances)
Univariate significance test
Newman-Keuls test (determination of significant differences)
Unequal N HSD test (multiple comparisons test).

The change in combability dK as a percentage can be calculated with use of the formula $dK = [(K_0 - K_i)/K_0] * 100$. $K_0$ in this case is the average value of the combability for undyed hair strands and $K_i$ the average value for the hair strands treated with the particular oxidative dyeing agent.

The care of the hair strands is the higher, the lower the applied combing force and thereby the higher the change in combing force. The dK values for the colors with use of cosmetic agents V1 and E2 are presented in Table 2. The coloring obtained with cosmetic agent E2 of the invention, which includes at least one special nonionic silicone polymer in a total amount of 0.5% by weight, in comparison with a coloring without nonionic silicone polymer (V1) has a greater change in combability and therefore improved care.

| Oxidative dyeing agents | dK [%] |
| --- | --- |
| V1 + O1 (1:1) | 36 |
| E2 + O1 (1:1) | 39 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic agent for changing the color of keratinic fibers, comprising, in a cosmetically acceptable carrier:

a) at least one compound, selected from the group consisting of oxidation dye precursors, direct dyes, and mixtures thereof,
b) 0.005 to 0.5% by weight, based on the total weight of the cosmetic agent, of at least one nonionic silicone polymer of the formula (III),

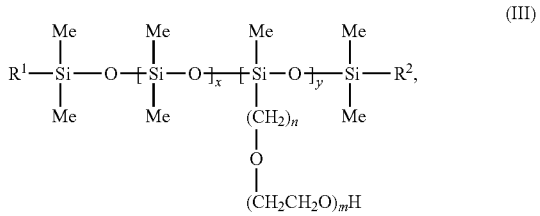

where
n stands for integers from 1 to 5,
m stands for integers from 2 to 20,
$R^1$ and $R^2$, in each case independently of one another, stand for a methyl group or a hydroxyl group, and
x and y, in each case independently of one another, stand for integers from 1 to 2000, and
wherein the at least one nonionic silicone polymer b) has an average molecular weight $M_w$ of 3000 to 100,000 Da.

2. The cosmetic agent according to claim 1, wherein the cosmetic agent further comprises polyoxyethylene (20) sorbitan monolaurate in a total amount of 0.003 to 1.5% by weight based on the total weight of the cosmetic agent.

3. The cosmetic agent according to claim 1, wherein the cosmetic agent further comprises polyoxyethylene (20) sorbitan monolaurate in a total amount of 0.015 to 0.3% by weight based on the total weight of the cosmetic agent.

4. The cosmetic agent according to claim 1, wherein the cosmetic agent in addition includes polyoxyethylene (7) lauryl ether in a total amount of 0.01 to 6% by weight based on the total weight of the cosmetic agent.

5. The cosmetic agent according to claim 1, wherein the cosmetic agent in addition includes polyoxyethylene (7) lauryl ether in a total amount of 0.05 to 1.5% by weight based on the total weight of the cosmetic agent.

6. The cosmetic agent according to claim 1, wherein the cosmetic agent further comprises at least one further compound, selected from the group consisting of: (i) thickeners; (ii) linear or branched, saturated or unsaturated alcohols having 8 to 20 carbon atoms; (iii) surfactants; (iv) alkalizing agents; (v) oils; and (vi) mixtures thereof.

7. The cosmetic agent according to claim 6, wherein cosmetic agent includes at least one thickener and the at least one thickener is at least one naturally occurring thickener, which is present in the cosmetic agent in a total amount of 0.0005 to 5.0% by weight, based on the total weight of the cosmetic agent.

8. The cosmetic agent according to claim 6, wherein the cosmetic agent includes at least one amphoteric surfactant, selected from amidopropyl betaines having 9 to 13 carbon atoms in the acyl group, and being included as a surfactant in a total amount of 0.1 to 5.0% by weight, based on the total weight of the cosmetic agent.

9. The cosmetic agent according to claim 6, wherein the cosmetic agent includes at least one alkalizing agent, said at least one alkalizing agent including at least two alkanolamines different from one another, in a total amount of 0.05 to 15% by weight, based on the total weight of the cosmetic agent.

10. The cosmetic agent according to claim 6, wherein the cosmetic agent includes at least one alkalizing agent, said at least one alkalizing agent including monoethanolamine and 2-amino-2-methylpropan-1-ol, a total amount 3.5 to 7.5% by weight, based on the total weight of the cosmetic agent.

11. A packaging unit, comprising, produced separately from one another,
a) at least one container (C1), containing a cosmetic agent according to claim 1, and
b) at least one container (C2), containing an oxidizing agent preparation, which in a cosmetically acceptable carrier includes at least one oxidizing agent in a total amount of 0.5 to 7.0% by weight, based on the total weight of the oxidizing agent preparation, and at least one acid.

12. A method for dyeing keratinic fibers with increased care with a simultaneously minimized color shift, wherein the method comprises the following process steps:
a) providing a cosmetic agent (M1) according to claim 1,
b) providing an oxidizing agent preparation (M2), including, in a cosmetically acceptable carrier, at least one oxidizing agent in a total amount of 0.5 to 7.0% by weight, based on the total weight of the oxidizing agent preparation, and at least one acid,
c) mixing the cosmetic agent (M1) with the oxidizing agent preparation (M2),
d) applying the mixture obtained in step c) to the keratinic fibers and leaving said mixture on the keratinic fibers for a time period of 10 to 60 minutes, at room temperature and/or at at least 30° C.
e) rinsing the keratinic fibers with water and/or a cleansing composition for 1 to 5 minutes, and
f) optionally applying an aftertreatment agent to the keratinic fibers and rinsing it off after a time period of 1 to 10 minutes.

* * * * *